(12) United States Patent
Zhang et al.

(10) Patent No.: US 11,590,178 B2
(45) Date of Patent: Feb. 28, 2023

(54) APPLICATION OF A BILE ACID COMPOSITE BACTERIAL AGENT IN THE PREPARATION OF FEED ADDITIVES FOR MUTTON SHEEP

(71) Applicant: Shandong Longchang Animal Health Product Co., Ltd., Shandong (CN)

(72) Inventors: Xilei Zhang, Shandong (CN); Aizhi Cao, Shandong (CN); Qianqian Lou, Shandong (CN); Limin Ji, Shandong (CN)

(73) Assignee: Shandong Longchang Animal Health Product Co., Ltd., Dezhou (CN)

( * ) Notice: Subject to any disclaimer, the term of this patent is extended or adjusted under 35 U.S.C. 154(b) by 0 days.

(21) Appl. No.: 17/511,544

(22) Filed: Oct. 26, 2021

(65) Prior Publication Data

US 2022/0152124 A1    May 19, 2022

(30) Foreign Application Priority Data

Nov. 19, 2020 (CN) .......................... 202011306541.9

(51) Int. Cl.
| | | |
|---|---|---|
| *A61K 35/74* | (2015.01) | |
| *A61K 39/02* | (2006.01) | |
| *A61K 35/00* | (2006.01) | |
| *A61K 35/741* | (2015.01) | |
| *A23K 50/10* | (2016.01) | |
| *A23K 10/18* | (2016.01) | |
| *A61K 9/00* | (2006.01) | |
| *A61K 31/575* | (2006.01) | |

(52) U.S. Cl.
CPC ............ *A61K 35/741* (2013.01); *A23K 10/18* (2016.05); *A23K 50/10* (2016.05); *A61K 9/0056* (2013.01); *A61K 31/575* (2013.01); *A61K 39/0216* (2013.01); *A61K 2035/115* (2013.01)

(58) Field of Classification Search
None
See application file for complete search history.

(56) References Cited

FOREIGN PATENT DOCUMENTS

CN        105851551 A        8/2016

OTHER PUBLICATIONS

Kai Wang et al., Parabacteroides Distasonis Alleviates Obesity and Metabolic Dysfunctions via Production of Succinate and Secondary Bile Acids, Cell Reports, Jan. 2, 2019, pp. 222-235 and e1-e5, vol. 26.

*Primary Examiner* — S. Devi

(57) ABSTRACT

The present invention discloses application of a bile acid composite bacterial agent in the preparation of feed additives for mutton sheep. The bile acid composite bacterial agent comprises *Parabacteroides distasonis* bacterial suspension and bile acid, and the *Parabacteroides distasonis* bacterial suspension is obtained by cultivation and fermentation of *Parabacteroides distasonis* LCG-06 with the deposit number CGMCC No. 20820. The bile acid composite bacterial agent of the present invention has natural components and has no toxic and side effects, and can significantly increase the growth rate of mutton sheep and promote nutrition absorption, accelerate the decomposition of in vivo fat of mutton sheep, thereby reducing the body fat percentage of mutton sheep, increasing the slaughter weight and slaughter rate of mutton sheep, increasing the incomes for breeding of mutton sheep. Therefore, it has broad application prospects.

3 Claims, 1 Drawing Sheet

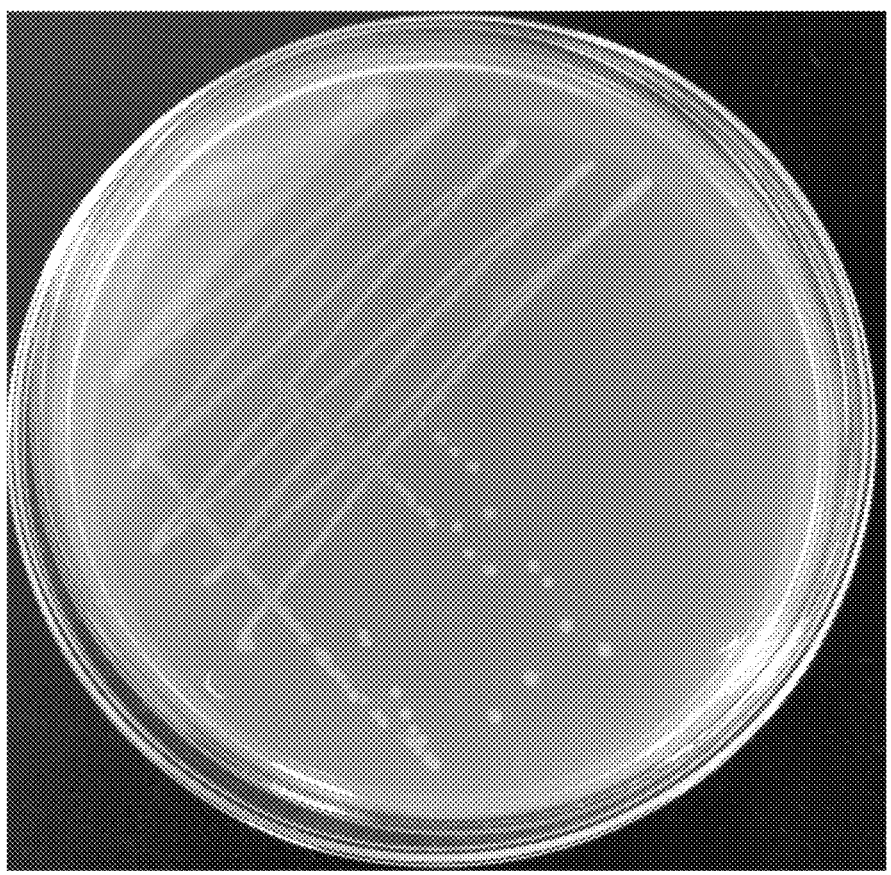

APPLICATION OF A BILE ACID COMPOSITE BACTERIAL AGENT IN THE PREPARATION OF FEED ADDITIVES FOR MUTTON SHEEP

CROSS-REFERENCE TO RELATED APPLICATIONS

The present application claims the benefit of Chinese Patent Application No. 202011306541.9 filed on Nov. 19, 2020, the contents of which are hereby incorporated by reference.

TECHNICAL FIELD

The present invention generally relates to the field of poultry and livestock breeding, and particularly to application of a bile acid composite bacterial agent in the preparation of feed additives for mutton sheep.

BACKGROUND

Mutton sheep is one of the most adaptable domestic animals to the external environment. With the improvement of the living standards of Chinese people, the demand for mutton sheep has gradually increased. Presently, allopatry fattening way is mainly adopted for mutton sheep. There are many ways for crops and livestock breeding. In the pasturing areas, due to prohibition and restriction of grazing, the feeding amount of ewes is reduced, leading to shortage of sheep. Moreover, due to lack of feeding standard, some fattening farms have no scientific feed ratio, which causes different sizes of mutton sheep. When there is lack of nutrition, yellow fat disease or increased fat content may occur, which will affect the quality of mutton sheep and the farming incomes of farmers. In addition, some veterinary drugs or other feed additives are used, which may have side effects and have residue in the body of mutton sheep. When people eat such mutton sheep, their health will be seriously threatened. Therefore, it is very necessary to develop an efficient natural bacterial agent that can improve the quality of mutton sheep.

SUMMARY

In order to solve the shortcomings of the prior art, the present invention provides application of a bile acid composite bacterial agent in the preparation of feed additives for mutton sheep. The bile acid composite bacterial agent can reduce body fat and slaughter weight of mutton sheep.

In order to achieve the object, the present invention adopts the following technical solutions:

The present invention provides a bile acid composite bacterial agent used as feed additives for mutton sheep, wherein the bile acid composite bacterial agent comprises a *Parabacteroides distasonis* bacterial suspension and bile acid.

Further, the *Parabacteroides distasonis* bacterial suspension is obtained by culture and fermentation of a *Parabacteroides distasonis* LCG-06, wherein the *Parabacteroides distasonis* LCG-06 was deposited at China General Microbiological Culture Collection Center (CGMCC) with the deposit number CGMCC No. 20820.

Further, the bacterial count of the bile acid composite bacterial agent is not less than $5 \times 10^8$ CFU/mL.

Further, the method of using the bile acid composite bacterial agent is: adding the bile acid composite bacterial agent to feeds for mutton sheep to feed for 20 to 40 consecutive days at an amount of 30 to 50 mL/sheep/day.

Further, the bile acid composite bacterial agent is added to feeds for mutton sheep at noon every day to feed mutton sheep.

Further, the bile acid composite bacterial agent can increase the slaughter weight and slaughter rate of mutton sheep.

A method for preparing a bile acid composite bacterial agent comprises the following steps:

(1) placing a *Parabacteroides distasonis* LCG-06 in a liquid nutrient medium and activating in an anaerobic environment at 37° C. for 40 to 48 h; adding a sucrose solution with mass concentration of 20% to the activated bacteria solution, mixing well and centrifuging to precipitate, adding a sucrose solution with mass concentration of 10% to the precipitate, resuspending uniformly to obtain a bacterial suspension of *Parabacteroides distasonis* LCG-06;

wherein the *Parabacteroides distasonis* LCG-06 was deposited at China General Microbiological Culture Collection Center (CGMCC) with deposit number CGMCC No. 20820;

(2) mixing the bacterial suspension of *Parabacteroides distasonis* LCG-06 with the bile acid uniformly to obtain a bile acid composite bacterial agent.

Further, the volume-to-mass ratio of the bacterial suspension of *Parabacteroides distasonis* LCG-06 to the bile acid is 8-10:1.

Further, the bacterial count of the bacterial suspension of *Parabacteroides distasonis* LCG-06 is not less than $2 \times 10^9$ CFU/mL.

Further, the bile acid contains no less than 78% hyocholic acid and hyodeoxycholic acid and no less than 18% chenodeoxycholic acid.

Compared with the prior art, the present invention has the following advantages and beneficial effects. In the present invention, a strain *Parabacteroides distasonis* LCG-06 is screened from the feces in the intestinal tract of pigs, which will not cause harm to animal and human body, and a sucrose solution is used to prepare *Parabacteroides distasonis* LCG-06 into a bacterial suspension, which is then compounded with bile acid in an optimized ratio to prepare a composite bacterial agent. The composite bacterial agent has natural components and has no toxic and side effects, and can significantly increase the growth rate of mutton sheep and promote nutrition absorption, accelerate the decomposition of in vivo fat of mutton sheep, thereby reducing the body fat percentage of mutton sheep, increasing the slaughter weight and slaughter rate of mutton sheep, increasing the incomes for breeding of mutton sheep. Therefore, it has broad application prospects.

BRIEF DESCRIPTION OF THE DRAWINGS

The sole FIGURE shows bacterial colonies of *Parabacteroides distasonis* LCG-06 on the TSA medium.

DETAILED DESCRIPTION

The technical solution of the present invention will be further described in detail below in conjunction with specific embodiments. The experimental methods that do not indicate specific conditions in the following examples are usually in accordance with conventional conditions or conditions recommended by the manufacturers.

Example 1

I. Screening and identification of *Parabacteroides distasonis* LCG-06

1. Screening of *Parabacteroides distasonis* LCG-06

Intestinal feces were taken from pig's intestines, 10 g of feces were mixed with 100 mL of sterile water, filtered to remove impurities and make a fecal diluent, and then sterile water was added to the diluent continuously, to make $10^{-1}$, $10^{-2}$, $10^{-3}$, $10^{-4}$, $10^{-5}$ diluents. Then $10^{-2}$, $10^{-3}$, $10^{-4}$, $10^{-5}$ diluents were spread on the Trypticase Soy Agar medium (TSA), and cultured at 37° C. for 4 days in an anaerobic environment containing 80% $N_2$, 10% $CO_2$, and 10% $H_2$. Obvious colonies were selected for multiple purifications to obtain a single colony, and named as LCG-06, and then placed in the TSA slant medium for refrigeration and storage. The formula of the TSA medium was as follows:

Tryptone 15.0 g, soytone 5.0 g, sodium chloride 5.0 g, agar 15.0 g, sterile water 1000 mL, pH 7.3±0.2.

As shown in the sole FIGURE, the biological characteristics of the bacterial colonies of the strain LCG-06 in TSA medium were as follows: circular or quasi-circular, milky white or off-white, flat, 0.2 to 1.8 mm in diameter, smooth and dull surface, semitransparent, with neat edges.

2. Identification of *Parabacteroides distasonis* LCG-06

The genomic DNA of the strain LCG-06 was extracted and used as a template to perform PCR amplification using 16S rRNA universal primers. The 16S rRNA amplified sequence was obtained and sequenced, and then the sequence Blast was performed. Results showed that the strain LCG-06 has the highest homology with *Parabacteroides distasonis* in the GenBank gene bank, so the strain LCG-06 was determined to be *Parabacteroides distasonis*.

The screened *Parabacteroides distasonis* LCG-06 was deposited in China General Microbiological Culture Collection Center (CGMCC) at Nio.3, 1 Beichen West Road, Chaoyang District, Beijing, Institute of Microbiology Chinese Academy of Sciences; the deposit date: Sep. 25, 2020; and the deposit No. of *Parabacteroides distasonis*: CGMCC No. 20820.

3. Preparation of Bacterial Suspension of *Parabacteroides distasonis* LCG-06

(1) Pick the deposited *Parabacteroides distasonis* LCG-06 into a liquid nutrient medium (tryptone 15.0 g, soytone 5.0 g, sodium chloride 5.0 g, sterile water 1000 mL, pH 7.4), activate and culture in an anaerobic environment at 37° C. for 48 h, to obtain bacterial solution of *Parabacteroides distasonis* LCG-06;

(2) Add 20% sucrose solution with a mass concentration to the bacterial solution at a volume ratio of 1:1, mix well, and centrifuge at 10,000 rpm/min for 5 min to obtain a bacterial strain precipitate;

(3) Re-dissolve the above bacterial strain precipitate with a sucrose solution with a mass concentration of 10% according to a ratio of the volume of the sucrose solution to the mass of the bacterial strain precipitate of 2:1, mix well to obtain the bacterial suspension of *Parabacteroides distasonis* LCG-06, with bacterial count of not less than $2 \times 10^9$ CFU/mL.

II. Preparation of Bile Acid

The process steps for preparing bile acid were as follows:

(1) Saponification: Add 1 kg of porcine gall powder crushed through a 40-mesh sieve into a reactor, then add 10 L of sodium hydroxide solution with a mass concentration of 10%, heat and stir until boiling, and keep boiling and stir for 14 h, then cool the saponification fluid until solid-liquid stratification, then remove the supernatant, to obtain the remaining solid of bile acid saponification product;

(2) Decolorization: Add 6 L of water to the bile acid saponification product, heat to 80° C. to completely dissolve the bile acid saponification product, then pour it into a decolorization tank, add 300 mL of hydrogen peroxide and stir evenly, react at room temperature for 24 h, then filter the reaction solution to an acidification tank, to obtain the filtrate;

(3) Acidification: Cool the filtrate to room temperature, slowly add a 10% hydrochloric acid solution, stir while adding, and stop adding acid when the pH of the solution reaches 3, and centrifuge and filter to obtain a white solid;

(4) Purification: Rinse the white solids with water continuously, to remove the water-soluble impurities attached to the surface of the white solids; after the filtered water is tested to be neutral, stop washing; place the white solids after centrifugal filtration into an oven, dry at 100° C. until less than 10% moisture, to obtain the crude bile acid;

(5) Recrystallization: Place the crude bile acid into an extraction tank, add ethyl acetate of 10 times the weight of the crude bile acid to stir until dissolved completely, then add 0.08 g of anhydrous sodium sulfate for dehydration, filter and collect the filtrate, concentrate the filtrate under reduced pressure and recover ethyl acetate to obtain liquid bile acid;

(6) Drying: Place the liquid bile acid into an oven and dry at 100° C. until no more than 1% moisture, to obtain a bile acid finished product.

The bile acid finished product contains 78.6% of hyocholic acid and hyodeoxycholic acid and 20.0% of chenodeoxycholic acid.

III. A Method for Preparing a Bile Acid Composite Bacterial Agent

The above prepared bile acid and bacterial suspension of *Parabacteroides distasonis* LCG-06 were mixed uniformly at a ratio of 1:10 (g/mL), to obtain a bile acid composite bacterial agent, with the total bacterial count of no less than $5 \times 10^8$ CFU/mL.

Example 2

Five hundred Boer goats were raised in a farm in Shandong, and 20 goats were randomly selected as the experimental group, and 20 goats as the control group, and all of 40 goats were of 4-5 generations. One month before the slaughter, the goats in the experimental group were fed with the feeds containing bile acid composite bacterial agent at noon every day, and the bile acid composite bacterial agent was evenly added to the feed at an additive amount of 30 to 50 mL per goat, and fed to goats continuously for 25 days. The goats in the control group were fed the same amount of feed, without adding bile acid composite bacterial agent. The feed was made of concentrated feed and grass feed in the same mixing ratio, and all mutton sheep continued to be raised in accordance with conventional breeding methods. 25 days later, goats were slaughtered, and the average slaughter weight of the mutton sheep in the control group was 56.44 kg, and more yellow and white fat was seen during slaughter; the average slaughter weight of the goats in the experimental group was 54.47 kg, with less yellow and white fat, and the mutton sheep in the experimental group had more weight gain during the 25-day breeding process, and higher average slaughter rate than that of the control group, indicating that the bile acid composite bacterial agent of the present invention can effectively reduce the body fat percentage of the mutton sheep, and increase the slaughter weight and average slaughter rate of mutton sheep.

|  | Initial average weight (kg) | Average slaughter weight (kg) | Weight gain (kg) | Body weight (kg) | Average slaughter rate (%) |
| --- | --- | --- | --- | --- | --- |
| Experimental group | 45.21 | 54.47 | 9.26 | 24.74 | 54.53 |
| Control group | 48.60 | 56.44 | 7.84 | 28.31 | 50.17 |

The above embodiments are only used to illustrate the technical solutions of the present invention rather than limit them; although the present invention has been described in detail with reference to the foregoing embodiments, those of ordinary skill in the art can make modifications to the technical solutions recorded in the foregoing embodiments or make equivalent replacement on some of the technical features; and these modifications or replacements shall not deviate from the spirit and scope of the technical solutions claimed by the present invention.

The invention claimed is:

1. A method for preparing a bile acid composite bacterial agent used as a feed additives for mutton sheep, comprising the following steps:
   (1) placing the *Parabacteroides distasonis* LCG-06 in a liquid nutrient medium and culturing the *Parabacteroides distasonis* LCG-06 in an anaerobic environment at 37° C. for 40 to 48 h; adding a sucrose solution with a mass concentration of 20% to the bacteria solution, mixing well and centrifuging to precipitate, resuspend the precipitate with a sucrose solution with a mass concentration of 10% to obtain a bacterial suspension of the *Parabacteroides distasonis* LCG-06;
   wherein the *Parabacteroides distasonis* LCG-06 was deposited at China General Microbiological Culture Collection Center (CGMCC) with the CGMCC deposit number 20820; and
   (2) mixing the bacterial suspension of the *Parabacteroides distasonis* LCG-06 with a bile acid uniformly to obtain the bile acid composite bacterial agent.

2. The method according to claim 1, wherein a volume-to-mass ratio of the bacterial suspension of the *Parabacteroides distasonis* LCG-06 to the bile acid is 8-10:1.

3. The method according to claim 1, wherein the bile acid contains no less than 78% by weight of hyocholic acid and hyodeoxycholic acid and no less than 18% by weight of chenodeoxycholic acid.

* * * * *